US012127494B2

(12) United States Patent
Yale et al.

(10) Patent No.: US 12,127,494 B2
(45) Date of Patent: Oct. 29, 2024

(54) ROBOTIC SYSTEM FOR AUTOMATED SOIL TESTING AND ANALYSES

(71) Applicant: Land Maverick LLC, Branford, CT (US)

(72) Inventors: Emily Yale, Branford, CT (US); Kevin Waugh, Astoria, NY (US); Ryan Ferreira, Stamford, CT (US); Jose Osorio, Norwalk, CT (US); John O'Neill, Abington, MA (US)

(73) Assignee: Land Maverick LLC, Branford, CT (US)

( * ) Notice: Subject to any disclaimer, the term of this patent is extended or adjusted under 35 U.S.C. 154(b) by 1085 days.

(21) Appl. No.: 16/385,290

(22) Filed: Apr. 16, 2019

(65) Prior Publication Data

US 2019/0313571 A1    Oct. 17, 2019

Related U.S. Application Data

(60) Provisional application No. 62/658,719, filed on Apr. 17, 2018.

(51) Int. Cl.
   *A01B 79/00*   (2006.01)
   *G01C 21/34*   (2006.01)
   (Continued)

(52) U.S. Cl.
   CPC ............ *A01B 79/005* (2013.01); *G01C 21/34* (2013.01); *G01N 33/24* (2013.01); *G01N 2001/021* (2013.01); *G01N 33/245* (2024.05)

(58) Field of Classification Search
   CPC ........... G01N 1/20; G01N 1/286; G01N 1/10; G01N 1/12; G01N 1/16; G01N 1/2273;
   (Continued)

(56) References Cited

U.S. PATENT DOCUMENTS

RE30,901 E  *  4/1982  Boxrud .................... G01N 1/08
                                                   73/864.45
6,016,713 A  *  1/2000  Hale ..................... A01B 79/005
                                                   73/864.45
(Continued)

FOREIGN PATENT DOCUMENTS

CN          104483285 A       12/2014
CN          107014976 A   *    8/2017
(Continued)

*Primary Examiner* — John E Breene
*Assistant Examiner* — Truong D Phan
(74) *Attorney, Agent, or Firm* — Ryan, Mason & Lewis, LLP (57) ABSTRACT

Methods, apparatus, and processor-readable storage media related to a robotic system for automated soil testing and analyses are provided herein. A computer-implemented method includes processing data pertaining to a given geographical region, generating one or more navigational courses within the given geographical region based at least in part on the processed data, and automatically collecting one or more soil samples at one or more predetermined locations within the given geographical region, in accordance with at least one of the generated navigational courses. Such a method also includes automatically analyzing the one or more collected soil samples based on one or more predetermined soil-related parameters, and generating and outputting results of the analyzing of the one or more collected soil samples.

20 Claims, 4 Drawing Sheets

(51) Int. Cl.
 *G01N 1/02* (2006.01)
 *G01N 33/24* (2006.01)
(58) Field of Classification Search
 CPC .. G01N 1/08; G01N 1/125; G01N 2001/1043;
  G01N 1/04; G01N 33/362; G01N 1/28;
  G01N 2001/021; G01N 2001/085; G01N
  2001/4061; G01N 2033/245; G01N
  33/24; E21B 49/025; E21B 49/02; E21B
  25/00; E21B 7/046; E21B 19/08; E21B
  7/021; E21B 7/02; E21B 7/26; B23Q
  5/265; B23Q 5/326; B23Q 16/003; E01C
  23/124; E04H 17/263; A01B 79/005;
  A01B 79/02; A01B 77/00; A01C 21/007;
  A01D 41/127; G01C 21/34; G01C 21/38;
  G01C 21/26; G01C 21/265; G01C 21/28;
  G01C 21/32; G01C 21/30; G01C
  21/3841; G01C 21/00; G01C 21/20
 See application file for complete search history.

(56) References Cited

U.S. PATENT DOCUMENTS

| | | | |
|---|---|---|---|
| 6,118,404 A * | 9/2000 | Fernekes | G01C 21/3667 |
| | | | 701/430 |
| 6,141,614 A | 10/2000 | Janzen et al. | |
| 6,518,765 B1 | 2/2003 | Gompf et al. | |
| 6,553,852 B1 * | 4/2003 | Smail | G01N 3/42 |
| | | | 73/866.5 |
| 10,244,675 B2 | 4/2019 | LaRowe | |
| 2003/0112152 A1 | 6/2003 | Pickett | |
| 2005/0165521 A1 * | 7/2005 | Gruhn | A01B 45/00 |
| | | | 701/29.5 |
| 2008/0142614 A1 * | 6/2008 | Elezaby | A01G 25/16 |
| | | | 239/69 |
| 2010/0037712 A1 * | 2/2010 | Burton | E21B 49/02 |
| | | | 53/284.7 |
| 2014/0345394 A1 * | 11/2014 | Schildroth | G01N 33/24 |
| | | | 73/863 |
| 2016/0377508 A1 * | 12/2016 | Perrone | G01M 17/06 |
| | | | 180/204 |
| 2018/0074499 A1 * | 3/2018 | Cantrell | G05D 1/0094 |
| 2018/0156697 A1 | 6/2018 | Fiechter | |
| 2018/0232578 A1 | 8/2018 | Pattnaik et al. | |

FOREIGN PATENT DOCUMENTS

| | | | | |
|---|---|---|---|---|
| CN | 107860892 A | | 11/2017 | |
| CN | 207650205 U | | 11/2017 | |
| CN | 107860892 | * | 2/2018 | |
| DE | 10214648 A1 | * | 10/2003 | ........... A01D 41/127 |
| EP | 1329148 | | 12/2001 | |
| EP | 1704766 A1 | | 3/2005 | |
| EP | 3200958 A1 | | 10/2014 | |
| JP | H11262310 A | * | 9/1999 | |
| JP | 2019002811 A | | 6/2017 | |
| KR | 20050080914 A | * | 8/2005 | |
| RO | 130710 | | 7/2015 | |
| RU | 168042 U1 | | 4/2016 | |

* cited by examiner

ROBOTIC SYSTEM FOR AUTOMATED SOIL TESTING AND ANALYSES

CROSS-REFERENCE TO RELATED APPLICATIONS

The present application claims priority to U.S. Provisional Application Ser. No. 62/658,719, filed Apr. 17, 2018, incorporated by reference herein.

FIELD

The field relates generally to information technology, and more particularly to robotics and agricultural technologies.

BACKGROUND

Land management industries face challenges in conducting large scale soil operations in a time and cost-effective manner. For example, golf course superintendents, farm operators, overseers, vineyard managers, landscapers, etc. often utilize a human actor using a hand probe to manually test soil for many parameters, including but not limited to, moisture and temperature. A verbal or hand-written report is commonly then generated, which can be vulnerable to inaccuracies and/or human error, with no efficient means to gather and correlate data over periods of time. A drone can also be used to gather soil data, but such a mechanism typically requires significant human intervention as well. Without the ability to accurately monitor soil parameters, such conventional approaches for various land management entities can lead to improper fertilizer choices, improper water usage, fertilizer timing, improper fertilizer volumes, improper fungicide choices, improper fungicide timing, and/or improper fungicide volumes. Additionally, over-application of fertilizer can cause problems such as fertilizer runoff, damage to crops, harm to surrounding livestock, and limited return-on-investment with respect to water, fertilizer and/or fungicide.

Accordingly, a need exists for accurate and cost-effective soil data obtainment and analysis techniques.

SUMMARY

Illustrative embodiments of the disclosure provide a robotic system for automated soil testing and analyses. An exemplary computer-implemented method includes processing data pertaining to a given geographical region, generating one or more navigational courses within the given geographical region based at least in part on the processed data, and automatically collecting one or more soil samples at one or more predetermined locations within the given geographical region, in accordance with at least one of the generated navigational courses. Such a method also includes automatically analyzing the one or more collected soil samples based on one or more predetermined soil-related parameters, and generating and outputting results of the analyzing of the one or more collected soil samples.

In another embodiment, an exemplary robotic system includes one or more power components, a drive train and steering system, one or more motors, at least one of one or more probes and one or more sensors, and a computing device comprises at least one processor operably coupled to a memory. In such a system, the computing device is configured for processing data pertaining to a given geographical region, generating one or more navigational courses within the given geographical region based at least in part on the processed data, and automatically collecting, via the at least one of the one or more probes and the one or more sensors, one or more soil samples at one or more predetermined locations within the given geographical region, in accordance with at least one of the generated navigational courses. Additionally, the computing device is also configured for automatically analyzing the one or more collected soil samples based on one or more predetermined soil-related parameters, and generating and outputting results of the analyzing of the one or more collected soil samples.

Illustrative embodiments can provide significant advantages relative to conventional soil testing approaches. For example, challenges associated with such approaches are overcome through temporally-efficient and accurate soil testing carried out automatically via a robotic system. Additionally, such a system is capable of acting in a fully autonomously fashion both during the day and at night. Further, such embodiments, as detailed herein, can include generating suggestions related to optimizing fertilization and/or watering practices, based on human-determined standards. The system is also able to automatically identify nutrients that are lacking in particular portions of soil and generating suggestions for remedying such deficiencies.

These and other illustrative embodiments described herein include, without limitation, methods, apparatus, networks, systems and processor-readable storage media.

DETAILED DESCRIPTION

As detailed herein, one or more embodiments include an autonomous robotic system designed to do perform soil sampling and related analytics, including but not limited to receiving input data about one or more desired conditions, collecting and/or analyzing data from one or more properties, comparing analysis results to the desired condition(s), and generating one or more suggestions pertaining to meeting the desired condition(s).

Example and/or illustrative embodiments will be described herein with reference to exemplary networks and associated computers, servers, network devices or other types of processing devices. It is to be appreciated, however, that the invention is not restricted to use with the particular illustrative network and device configurations shown. By way of example, the term "network" as used herein is intended to be broadly construed, so as to encompass, for example, any system comprising multiple networked processing devices.

Figure 1:
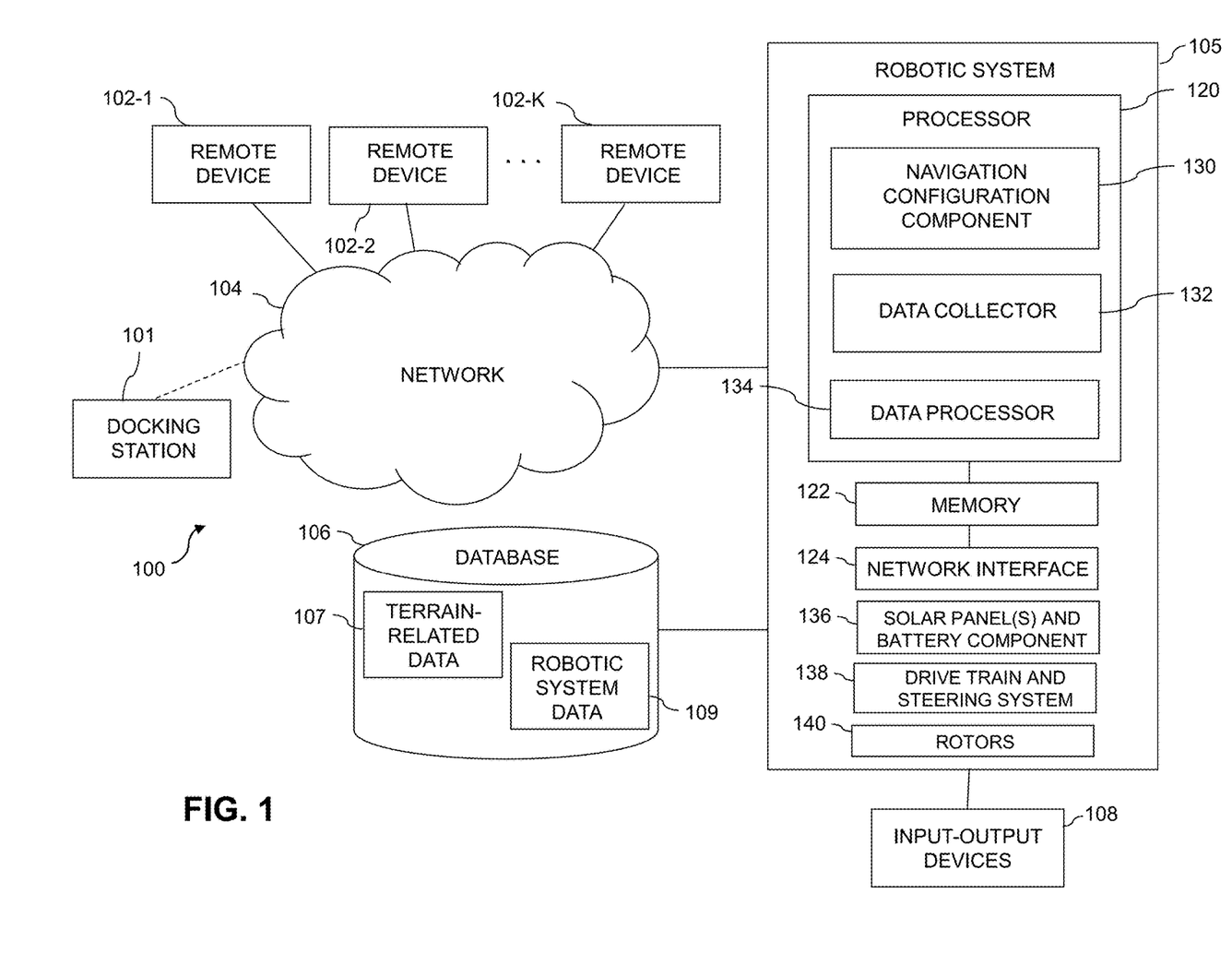
FIG. 1 is a block diagram of a network configured for implementation of a robotic system for automated soil testing and analyses in an example embodiment.

FIG. 1 shows a network 100 configured in accordance with an example embodiment. The network 100 includes a plurality of remote devices 102-1, 102-2, . . . 102-K, collectively referred to herein as remote devices 102. The remote devices 102 are coupled to a network 104, where the network 104 in such an embodiment is assumed to represent a sub-network or other related portion of the larger network 100. Accordingly, elements 100 and 104 are both referred to herein as examples of "networks," but element 104 is assumed to be a component of element 100 in the context of the FIG. 1 embodiment. Also coupled to the network 104 is robotic system 105.

The remote devices 102 can include, for example, one or more servers (associated with the robotic system 105). The remote devices 102 can also include, for example, user devices such as computers, mobile devices, smart phones, tablets, etc. Such devices 102 can also be enhanced with the addition of a controller and/or joystick. Alternatively, in one or more embodiments remote devices 102 can include remote controllers and/or joysticks. The remote devices 102, as illustrated in FIG. 1, can connect (wirelessly or via a hard-wired connection) to the robotic system 105 via network 104. Accordingly, an example embodiment such as depicted in FIG. 1 includes a user interacting with the robotic system 105 via a software application resident on the user's remote device 102 (such as a tablet, a smart phone, a laptop, a desktop computer, etc.).

Referring again to FIG. 1, in one or more embodiments, each remote device 102 is assumed to be implemented using at least one processing device. Each such processing device generally includes at least one processor and at least one associated memory, and implements one or more functional software modules or components for controlling certain features of the remote device 102.

Similarly, in at least one embodiment, the robotic system 105 in the FIG. 1 embodiment can be implemented using at least one processing device. Each such processing device can include at least one processor and at least one associated memory, and can implement one or more functional software modules or components for controlling certain features of the robotic system 105. Also, in at least one embodiment, the robotic system 105 can be coupled to a power source and/or contain a power source (such as a battery) therein. Additionally, the robotic system 105 can include a mechanism 136 to charge such a power source (such as a battery, for example) via a power cord, inductive charging, one or more solar panels, etc. Charging via solar panels can be carried out, for example, while the robotic system 105 is collecting soil data. As noted, the robotic system 105 is also capable of charging via power cord, inductive charging, etc. in connection with a docking station 101 (e.g., a separate structure and/or device). The docking station 101 is capable of indicating the battery status of the robotic system 105.

Additionally, in one or more embodiments, the docking station 101 is able to protect the robotic system 105, while engaged with the robotic system 105, from weather elements such as rain, wind, hail, etc. The docking station 101, which can optionally be connected to network 104 via a wireless or wired connection, or a remote user can signal the robotic system 105 to return to the docking station 101, for example, in times of inclement weather, when the battery and/or power level of the robotic system 105 has descended below a given threshold amount, etc. The robotic system 105 (in conjunction with the database 106, for example) can, in such an embodiment, determine and/or compute the shortest route for the robotic system 105 to navigate to return to the docking station 101. In at least one embodiment, the robotic system 105 can also be configured to accept notifications from one or more location alert systems, which can also trigger a return to the docking station 101.

In the example embodiment illustrated in FIG. 1, the robotic system 105 includes a processor 120 coupled to a memory 122 and a network interface 124.

The processor 120 can include, for example, a microprocessor, a microcontroller, an application-specific integrated circuit, a field-programmable gate array or other type of processing circuitry, as well as portions or combinations of such circuitry elements.

The memory 122 can include, for example, random access memory (RAM), read-only memory (ROM) or other types of memory, in any combination. The memory 122 and other memories disclosed herein can also be viewed as examples of processor-readable storage media, which can store executable computer program code and/or other types of software programs.

Examples of such processor-readable storage media can include, by way merely of example and not limitation, a storage device such as a storage disk, a storage array or an integrated circuit containing memory, as well as a wide variety of other types of computer program products. The term "processor-readable storage media" as used herein should be understood to exclude transitory, propagating signals.

The network interface 124 allows the robotic system 105 to communicate over the network 104 with the remote devices 102, and can include, for example, one or more conventional transceivers.

Additionally as detailed herein, the remote devices 102 can be coupled to one or more additional devices such as mobile telephones, laptop computers, tablet computers, desktop computers, remote controls, joysticks, or other types of computing devices.

The remote devices 102, in one or more embodiments, can be coupled to respective computers or devices associated with a particular company, organization or other enterprise. In addition, at least portions of the network 100 may also be referred to herein as collectively comprising an "enterprise network." Numerous other operating scenarios involving a wide variety of different types and arrangements of processing devices and networks are possible, as will be appreciated by those skilled in the art.

Also, it is to be appreciated that the term "user" herein is intended to be broadly construed so as to encompass, for example, human, hardware, software or firmware entities, as well as various combinations of such entities.

The network 104 is assumed to include a portion of a global computer network such as the Internet, although other types of networks can be part of the network 100, including a wide area network (WAN), a local area network (LAN), a satellite network, a telephone or cable network, a cellular network, a wireless network such as a Wi-Fi or WiMAX network, Bluetooth network, or various portions or combinations of these and other types of networks. Also, the network 100, in one or more embodiments, can include combinations of different types of networks, each including processing devices configured to communicate using internet protocol (IP) or other related communication protocols.

The robotic system 105 has an associated database 106 configured to store data related to soil testing operations. The database 106 more particularly stores terrain-related data 107, which can include geographic boundary data and/or grid information, property data (including identification and/or description of sub-regions of a property), collected soil sample information, processed soil sample information, etc. Geographic boundary data can include, for example, the parameters of the property that the robotic system 105 will test. Property data can include, for example, the identification (and location) of objects such as but not limited to sprinkler heads, bodies of water, sand traps, rocks, trees, shrubs, patios, out buildings, etc. Sub-regions of a property typically include smaller labeled sections that can be sampled (by the robotic system 105) individually or in different combinations. Such sections can include, for example, greens, tees, fairways, lower fields, upper fields, north fields, south fields, west fields, east fields, etc. By way of specific example, for golf courses, the ability to select sub-regions and select the time that testing (by the robotic system 105) is to be conducted is extremely valuable. The ability for the robotic system 105 to operate, for example, on a golf course, autonomously, both during the day and at night, without need of human monitoring provides numerous benefits over conventional systems and approaches.

Additionally, the database 106 also stores robotic system data 109, which can include information pertaining to the functioning and operations carried out by the robotic system 105. The database 106 can also contain information on how to process and display information on one or more remote devices 102. The processing and displaying of information incorporates comparing the received input data about desired conditions to data collected from the property by the robotic system 105. The database 106 also includes information related to generating suggestions on how to adjust one or more conditions pertaining to the soil in question based at least in part on the comparison of the collected soil data to the desired conditions.

Also, in one or more embodiments, the robotic system 105 and database 106 are capable of creating a feedback loop such that when the robotic system 105 generates a suggestion pertaining to modifying one or more soil-related conditions, and the suggestion is executed but the desired result is not achieved, the robotic system 105 is capable of establishing a correction factor. This correction factor is then applied to the next set of one or more suggestions that the robotic system 105 generates. Such a mechanism is an active feedback loop that allows for continuous adjustment to the correction factor.

In at least one embodiment, database 106 can be implemented using one or more storage systems associated with the robotic system 105. Such storage systems can comprise any of a variety of types of storage including network-attached storage, storage area networks, direct-attached storage and distributed direct-attached storage, as well as combinations of these and other storage types, including software-defined storage. Additionally, in one or more embodiments, the database 106 itself can be hosted on a network.

Also associated with the robotic system 105 are input-output devices 108, which can include, by way merely of example, keyboards, controllers, joysticks, displays or other types of input-output devices in any combination. Such input-output devices can be used to support one or more user interfaces (UIs) to the robotic system 105, as well as to support communication between the robotic system 105 and other related systems and devices not explicitly illustrated in FIG. 1.

Referring again to the depiction of robotic system 105, the processor 120 can also include a navigation configuration component 130, a data collector 132, and a data processor 134.

It is to be appreciated that this particular arrangement of modules 130, 132 and 134 illustrated in the processor 120 of the FIG. 1 embodiment is presented by way of example only, and alternative arrangements can be used in one or more other embodiments. For example, the functionality associated with the modules 130, 132 and 134 in other embodiments can be combined into a single module, or separated across a number of modules. By way of further example, multiple distinct processors can be used to implement different ones of the modules 130, 132 and 134, or portions thereof. In one or more embodiments, the data collector 132 can be mounted on one or more carriers for deployment. Such carriers can include linear actuators, servomotors, rotary systems, etc.

Also, at least portions of the navigation configuration component 130, data collector 132, and data processor 134 can be implemented at least in part in the form of software that is stored in memory 122 and executed by processor 120.

Further, an example process utilizing navigation configuration component 130, data collector 132, and data processor 134 of the robotic system 105 in network 100 is described below, including in connection with the description of FIG. 4.

The robotic system 105 also includes a drive train and a steering system 138 that allow the robot to move and navigate a property. Such a drive train and steering system 138 can include, for example (and as further detailed in connection with FIG. 2 and FIG. 3), one or more wheels, a suspension system, one or more lower control arms, one or more upper control arms, shocks, one or more stabilizing arms, one or more anti-roll bars, one or more suspension limiters, and one or more sway bars. The steering system can include, for example, a rack and pinion, one or more tie rods, one or more hiem joints, and one or more other articulating joints that allow the one or more wheels to turn left and right in a controlled fashion. Further, the robotic system 105 is powered by at least one motor. Also, at least one embodiment includes at least one sensor to check and/or determine the position (and/or functional status) of the steering system. It is also to be appreciated that the robotic system 105 can be configured such that any number of wheels can turn or be in a fixed position parallel to the body of the robot (body).

In one or more embodiments, the robotic system 105 can also include one or more rotors 140 or other subsystems that are capable of vertical flight. Such components allow the robotic system 105 to change the amount of mass, or normal force, that the robotic system 105 applies to the ground. The robotic system 105, in such an embodiment, has sufficient control capabilities to maintain all wheels in contact with the ground while the rotors 140 are operating. When the rotors 140 are engaged to lower the normal force on the ground, the robotic system 105 is still able to use the wheels, axles, motors, and gearboxes to drive/move forwards, backwards, left and/or right. That is, the rotors 140 do not take over the control of that type of motion when engaged to lower the normal force the robotic system 105 applies to the ground. Such an embodiment allows the robotic system 105, for example, to traverse mud, puddles, etc. Additionally, in at least one embodiment, the rotor(s) 140 and/or other vertical flight-capable subsystem(s) can be engaged and cause the robotic system 105 to achieve vertical flight.

It is to be understood that the particular set of elements shown in FIG. 1 for automatically conducting soil testing operations and analyses involving remote devices 102 of network 100 is depicted by way of illustrative example only, and in one or more other embodiments, additional or alternative elements may be used.

By way merely of example, in one or more other embodiments, the robotic system 105 can be eliminated and associated elements such as navigation configuration component 130, data collector 132, and data processor 134 can be implemented elsewhere in network 100.

Figure 2:
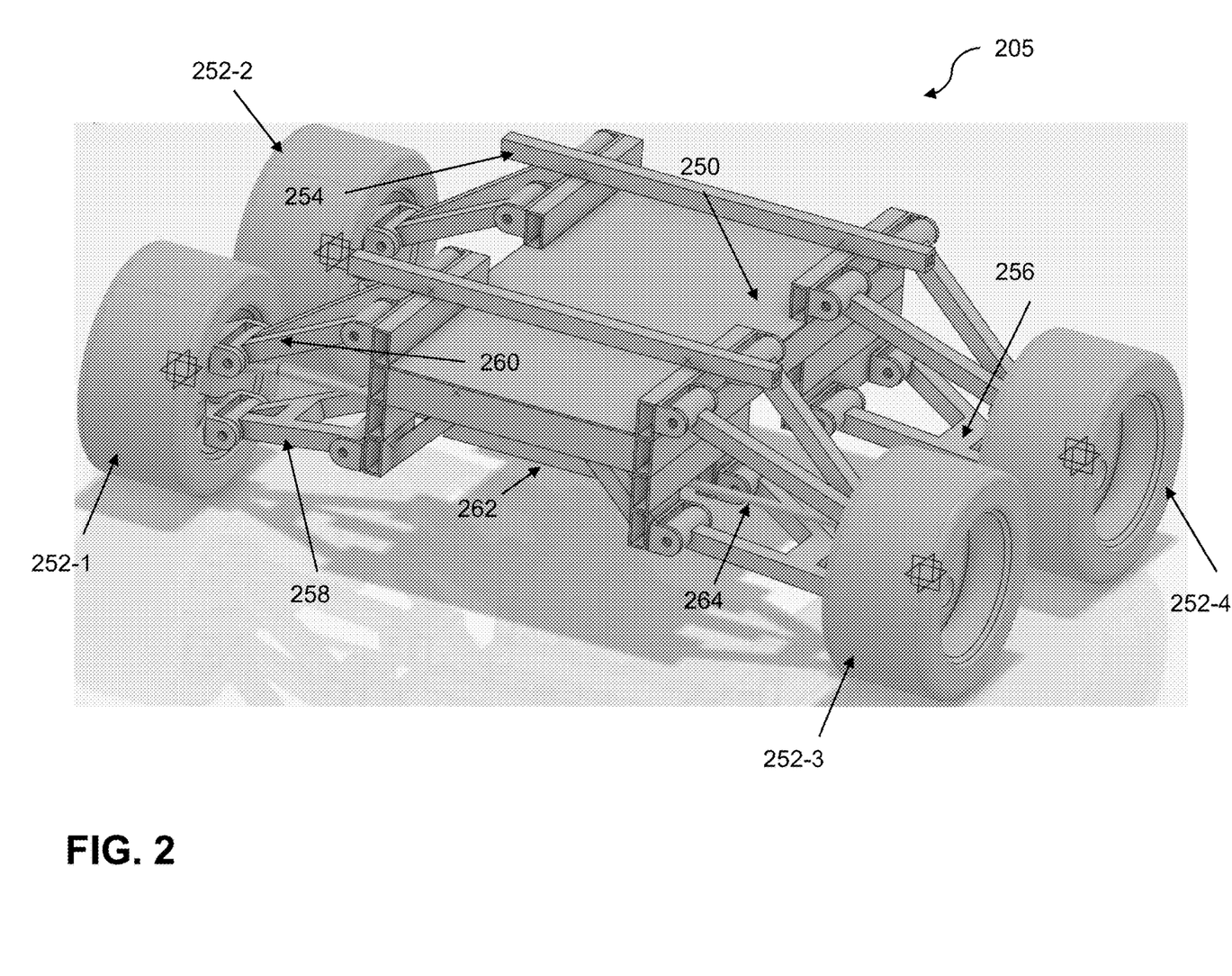
FIG. 2 is a system diagram illustrating at least a portion of a robotic system for automated soil testing and analyses in an example embodiment.

FIG. 2 is a system diagram illustrating at least a portion of a robotic system for automated soil testing and analyses in an example embodiment. By way of illustration, FIG. 2 depicts robotic system 205, and more specifically, various physical components thereof. For example FIG. 2 depicts frame 250, wheels 252-1, 252-2, 252-3 and 252-4 (though it should be noted that while FIG. 2 depicts an example embodiment containing four wheels, one or more alternate embodiments can include different numbers of wheels), shock tower 254, lower shock mount 256, lower suspension arm 258, upper suspension arm 260, steering rack 262, and tie rod 264.

In the example embodiment depicted in FIG. 2, the frame 250 is designed to hold multiple components and protect such components from various impacts (such as, for example, being struck by rocks). The wheels 252-1, 252-2, 252-3 and 252-4 are designed to carry the robotic system 205 and ease traveling. The shock tower 254 represents the mounting point for the top of the shock, while the lower shock mount 256 is the mount for the bottom of the shock. The lower suspension arm 258 connects a low point on the frame 250 to the bottom of a wheel knuckle/hub. The upper suspension arm 260 connects to a high point on the frame 250 and to the top of a wheel knuckle/hub. The steering rack 262 attaches to a tie rod 264 on either side (of the steering rack 262), and each tie rod 264 additionally attaches to the wheels 252-1, 252-2, 252-3 and 252-4. This suspension system (as depicted in the example embodiment of FIG. 2) is also referred to as a double wishbone suspension system, but it is to be appreciated that other suspension configurations (such as MacPherson strut, independent, trailing arm, semi-trailing arm, etc.) could be used in accordance with one or more embodiments.

Figure 3:
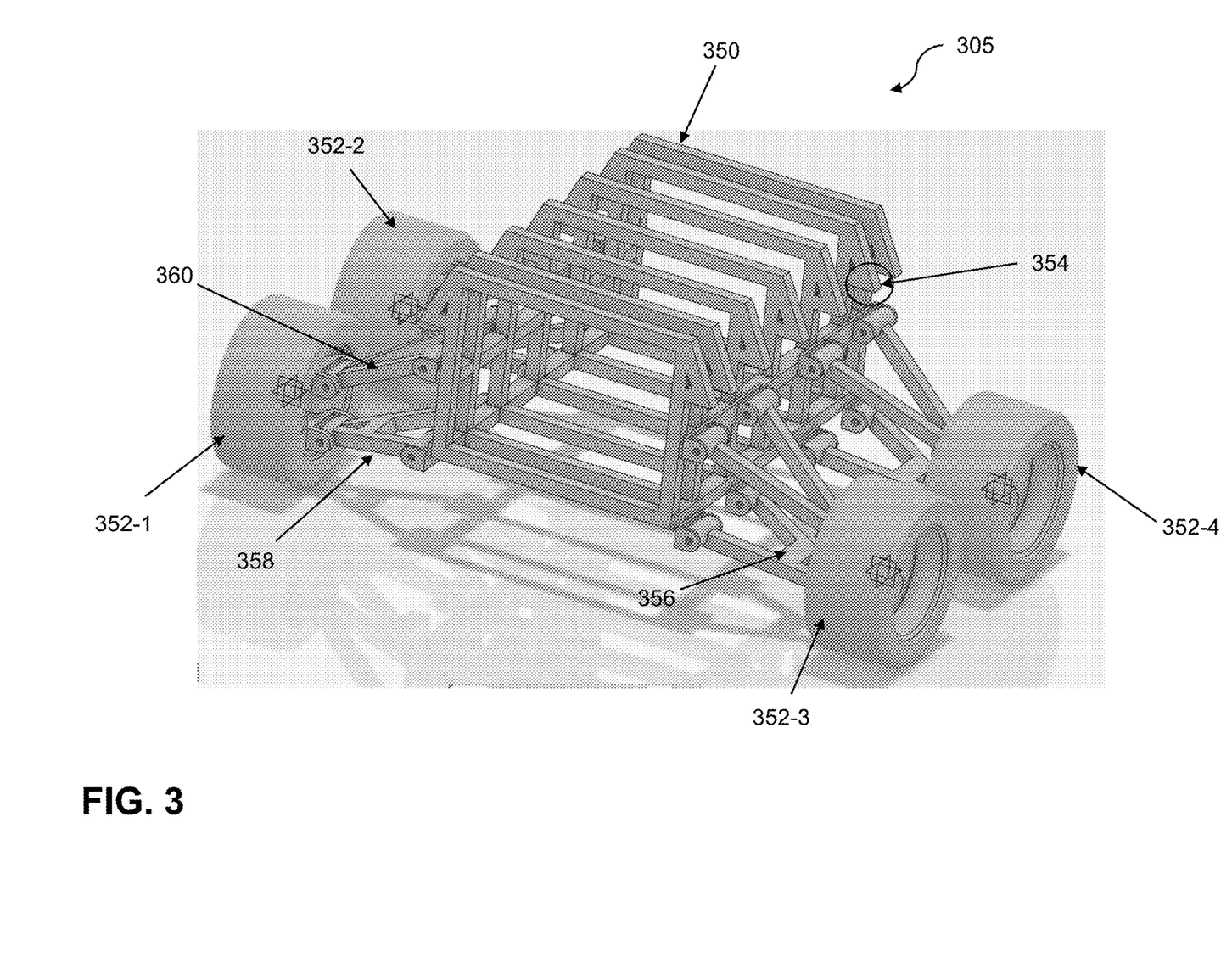
FIG. 3 is a system diagram illustrating at least a portion of a robotic system for automated soil testing and analyses in an example embodiment.

FIG. 3 is a system diagram illustrating at least a portion of a robotic system for automated soil testing and analyses in an example embodiment. By way of illustration, FIG. 3 depicts robotic system 305, and more specifically, various physical components thereof. For example, similar to the example embodiment depicted in FIG. 2, FIG. 3 depicts frame 350, wheels 352-1, 352-2, 352-3 and 352-4 (though it should be again noted that while FIG. 3 depicts an example embodiment containing four wheels, one or more alternate embodiments can include different numbers of wheels), shock tower 354, lower shock mount 356, lower suspension arm 358, and upper suspension arm 360.

By way of example and contrast, it is noted that FIG. 2 depicts a robotic system 205 configured with a significant amount of ground clearance, while FIG. 3 depicts a robotic system 305 with a large protected volume and a lower ground clearance.

Additionally, in one or more embodiments, a mount for one or more probes can be configured to allow the one or more probes to extend out of and/or below the robotic system body (when taking measurements, for example) and to retract inside of the robotic system body (when not actively taking measurements, for example). Such probes can be mounted, for instance, in the frame (such as 250 in FIGS. 2 and 350 in FIG. 3, for example) of the robotic system in an area inside of the suspension mounts. Different probes may be mounted in a rigid or movable fashion outside of the of the robotic system perimeter, and such probes can be mounted on the outer edges of the frame (250 or 350, e.g.) in a manner that does not interfere with the suspension system or steering system. In such an embodiment, a multitude of types of sensors can be used to collect and/or analyze soil-related data.

Accordingly, at least one embodiment includes generating and/or implementing an autonomous robotic system configured to perform mass soil sampling on various types of terrain. In such an embodiment, the robotic system can be configured to operate on the global positioning system (GPS) system, and the perimeter/boundary of the property to be tested and/or monitored, specific sub-regions thereof, as well as any hazards and/or physical landmarks or salient features, can be programmed into the robotic system. One or more embodiments can then include analyzing the input/programmed perimeter/boundary of the property, and determining and/or generating a grid or path with specific test points on the property based on this analysis. Additionally, in such an embodiment, the robotic system is capable of processing data from sensors resident therein/thereon regarding hazards in the local environment such as rocks, trees, water, livestock, humans, etc., and modifying a navigational path in response thereto. Such sensors can include but are not limited to proximity sensors, ultrasonic sensors, LIDAR sensors, laser sensors, infrared sensors, thermal sensors, etc.

Additionally, such sensors can be used in a dual purpose as a safety and security system for the robotic system 105. Using such sensors, the robotic system 105 can track its proximity to the ground, and if that measure/number changes rapidly, the robotic system 105 can deduce that it is being lifted (and potentially generate an alarm and/or notification to this extent).

Further, such an embodiment can additionally include performing one or more soil tests at given grid- or path-related increments such as, for example, at each node in the grid or path, at every second node in the grid or path, etc. Additionally, at least one embodiment can include programming the robotic system 105 to run automatically on a temporally-based schedule, to run upon manual activation, and/or to run automatically upon a triggering event. Also, in one or more embodiments, the robotic system 105 is capable of being controlled directly via a remote control.

In one or more embodiments, the robotic system can be controlled through a software application (app) (installed on a remote device such as, for example, remote device 102) by a remote user (such as, for example, the superintendent of a golf course, farm operators, overseers, vineyard managers, landscapers, etc.). By way of example, the remote user can receive, via the app, a notification (generated by the robotic system, a database and/or a server associated with the robotic system) querying the remote user to schedule a testing run for the robotic system. In such an example embodiment, the remote user can supply (to the robotic system, a database and/or a server associated with the robotic system) a time at which the robotic system is to start testing, the grid size or path size over which the robotic system is to test soil, and the particular parameters for which the robotic system is to test. Such tests can include, by way merely of example, moisture tests, temperature tests, pH tests, phosphorus level tests, nitrogen level tests, potassium level tests, and calcium level tests.

Subsequent to the robotic system carrying out the above-described testing, the robotic system, a database and/or a server associated with the robotic system will generate and send to the remote user a report detailing the results of the testing (such as the selected nutrient levels at various points/nodes in the grid or path, the moisture content of the soil at various points/node in the grid or path, etc.). The remote user is able to select what time this data will be sent (to him or her). In one or more embodiments, the data can be packed and sent at a specific set time, periodically, or sent as soon as the data are collected and/or analyzed.

Alternatively, in one or more embodiments, the robotic system can be controlled through a server (an example of a remote device 102, as illustrated in FIG. 1) associated with the robotic system. In such an embodiment, the server can provide the scheduling inputs to the robotic system and received the testing results directly from the robotic system. The server can then force data out to the remote user.

In one or more embodiments, the stored data can be configured in such a manner that all data used to make management decisions during a given temporal period (such as that day) are marked accordingly on the end user application. For example, if the end user (such as a golf course manger or superintendent) needs data from Apr. 1, 2019 at 10:00 PM through Apr. 2, 2019 at 9:59 PM to make one or more management decisions about how to use resources on the property on Apr. 2, 2019, then all data in the noted temporal window can be brought up and/or presented when the end user selects Apr. 2, 2019.

In at least one embodiment, the robotic system can include one or more probes for testing parameters such as, for example, soil temperature, moisture content, various nutrient levels, etc. Additionally, the robotic system also includes a wheel base and one or more control mechanisms (which can be configured and operated remotely, for example). Also, mechanical components of the robotic system can include a rover body, a chassis, and one or more mounts for the one or more probes, one or more sensors, and one or more data storage devices. In one or more embodiments, a mount for a probe can be configured to allow the probe to extend out of and/or below the rover body (when taking measurements, for example) and to retract inside of the rover body (when not actively taking measurements, for example). Additionally, in at least one embodiment, different probes may be mounted on and/or in the robotic system in a rigid or movable fashion.

The body of the robotic system can be constructed, for example, from materials such as aluminum, composites, and/or plastics. The robotic system can be constructed using welds, bolts, rivets, fusion pieces of material, etc. Further, in one or more embodiments, the robotic system includes one or more wheels (such as four wheels as depicted in FIG. 2 and FIG. 3, for example), and the robotic system's motion can be enabled and/or facilitated via components such as one or more pneumatic actuators, one or more linear systems, one or more rotary systems, etc. Additionally, in at least one embodiment, the robotic system also includes one or more motors, axels, shocks, gear boxes, lower control arms, upper control arms, shocks, stabilizing arms, anti-roll bars, suspension limiters, and/or sway bars. The steering system of such an embodiment is comprised of components such as a rack and pinion, tie rods (such as depicted as component 264 in FIG. 2, for example), hiem joints, and/or one or more other articulating joints that allow the wheels (such as depicted in FIG. 2 and FIG. 3, for example) to turn left and right in a controlled fashion. In such an embodiment, the robotic system is powered by at least one motor. Also, such an embodiment includes at least one sensor to check or determine the position of the steering system, and/or check or determine the functional status of the steering system. Additionally, the robotic system can be configured such that any number of wheels can turn or be in a fixed position parallel to the body of the robotic system.

In at least one embodiment, electrical components the robotic system can include one or more probes and/or one or more sensors (electronic sensors, for example), as well as a wiring harness to connect the one or more probes, the one or more sensors, the drive system, and one or more onboard computers (that is, one or more processors coupled to one or more memories). Such sensors, as detailed herein, can be responsible for conducting soil testing as well as other related functions. For example, one or more embodiments can include incorporating (into the robotic system) additional and/or different sensors in order to collect different data for distinct and/or specific testing applications.

Also, the one or more sensors can include, for example, one or more navigation-related sensors that can assist in navigating the robotic system within particular geographic boundaries, as well as in avoiding various obstacles (such as humans, golf carts, golf bags, tractors, mowers, livestock, fence posts, rocks, water hazards, etc.). Accordingly, in one or more embodiments, the robotic system is capable of passively and/or actively avoiding humans. Also, in at least one embodiment, remote users of the robotic system are capable of implementing an emergency stopping of the robotic system (by submitting an instruction, pushing a relevant button, etc. via a remote device). Active avoidance can involve the robotic system driving away from the human (or other obstacle), while passive avoidance can involve the robotic system ceasing movement until the human (or other obstacle) is a sufficient distance away.

By way of example, in at least one embodiment, the robotic system can use one or more ultrasound sensors, one or more proximity sensors, one or more infrared sensors, and/or one or more vision sensors to avoid navigating into obstacles and/or hazards. Such an example robotic system can also use GPS, long-term evolution (LTE), and pre-programmed information to determine a path by which the robotic system will travel across/within a given terrain, grid, and/or path. In one or more embodiments, the robotic system can also identify objects (such as golf balls, golf tees, sticks, etc.) that, if run over, would cause damage to the ground and/or grass.

In addition to avoiding specific obstacles, the robotic system is also capable of driving towards objects using one of more sensors (such as the sensors detailed herein). The robotic system can be configured to follow a piece of equipment (such as, for example, a mower or a tractor) to guide the robotic system along a path. Additionally, in one or more embodiments, the robotic system is configured to disrupt and/or alarm undesirable animals (such as geese, squirrels, raccoons, etc.) from properties. In such an embodiment, the robotic system is configured and/or programmed with a profile of one or more undesirable animals and how to detect them based on types of data captured by one or more sensors. Upon such a discovery and/or determination, the robotic system can navigate towards the identified animal and/or emit a noise or signal (such as flashing lights, for example,) to deter the identified animal.

Additionally, in one or more embodiments, software components of the robotic system can be configured to carry out a data collection sub-routine, a data processing sub-routine, and a maintenance sub-routine. In such an embodiment, a data collecting sub-routine can include programing the robotic system to drive autonomously inside an operator-defined set of geographic boundaries, follow a selected object and/or human, select different testing nodes inside of the boundaries, correct robotic system movement based on sensed sensor data, deploy probes for testing at the selected testing nodes, and store data obtained from the probes.

Further, in such an embodiment, a data processing sub-routine can include processing the stored data in accordance with one or more predefined algorithms and/or one or more data models, and generating and outputting at least a portion of the processed data to a remote user (via a software application on a user device) and/or a server associated with the robotic system. By way of example, the robotic system can process the obtained/collected data, and based thereon, generate a visual representation of the terrain in question with respect to one or more relevant parameters and/or variables.

Additionally, in at least one embodiment, a maintenance sub-routine can involve the robotic system returning to its charging station (which can be included as part of docking station 101, for example) to be charged via a power cord and/or inductive charging mechanism (including, for example component 136). The charging station, as detailed herein, can include an indicator system capable of identifying the charge status of the batteries of the robotic system. Also, in one or more embodiments, the robotic system can be configured to charge via one or more solar panels (affixed and/or connected to the robotic system) while in operation. Additionally, the charging station can be configured to include one or more solar panels, one or more wind turbines, and/or other renewable power generation system.

By way of another example, in one or more embodiments, the robotic system can collect and analyze soil samples, save the corresponding soil sample data to a memory with related information such as time, location, latitude, longitude, hole number, specific region or sub-region, sample number, results description, etc. Subsequently, the soil sample data can be utilized to generate (via a software application) a heat map representing one or more relevant portions of the terrain in question. Such a software application is also capable of over-laying one or more other key features to the specific section of the property such as, but not limited to, sprinkler locations, tee locations, green locations, hazard locations, etc. Further, such an embodiment can, based on the soil sample data, generate a report on modifying and/or establishing use parameters for one or more sprinklers associated with the terrain in question.

Accordingly, in one or more embodiments, the robotic system can generate one or more suggestions, based on analysis of testing results, pertaining to watering and/or sprinkling use related to the terrain subject to the testing. The system can also determine and/or generate suggestions pertaining to fertilizer and/or fungicide usage. For example, in such an embodiment, the robotic system can generate and output (to a remote user and/or a server associated with the robotic system) a suggestion of a duration of time for which a particular set of sprinklers should run in each of one or more regions or zones of the terrain in question, in order to bring the relevant soil to a given moisture level (based on user input related to desired moisture level, for example). In one or more embodiments, the robotic system is also capable of learning and adapting one or more suggestions based on the results of analyses such as noted above. For example, if the property sampled at level X for a given parameter, and the robotic system suggested to turn one or more relevant sprinklers on for Y minutes with the expectation that the property would reach level Z for the given parameter, but then the robotic system subsequently samples the property and determines that the property has only reached level A for the given parameter, the robotic system (and/or database and/or remote device/server linked to the robotic system) processed that information and uses the information to generate one or more adjustments for the next application/iteration of suggestions.

Figure 4:
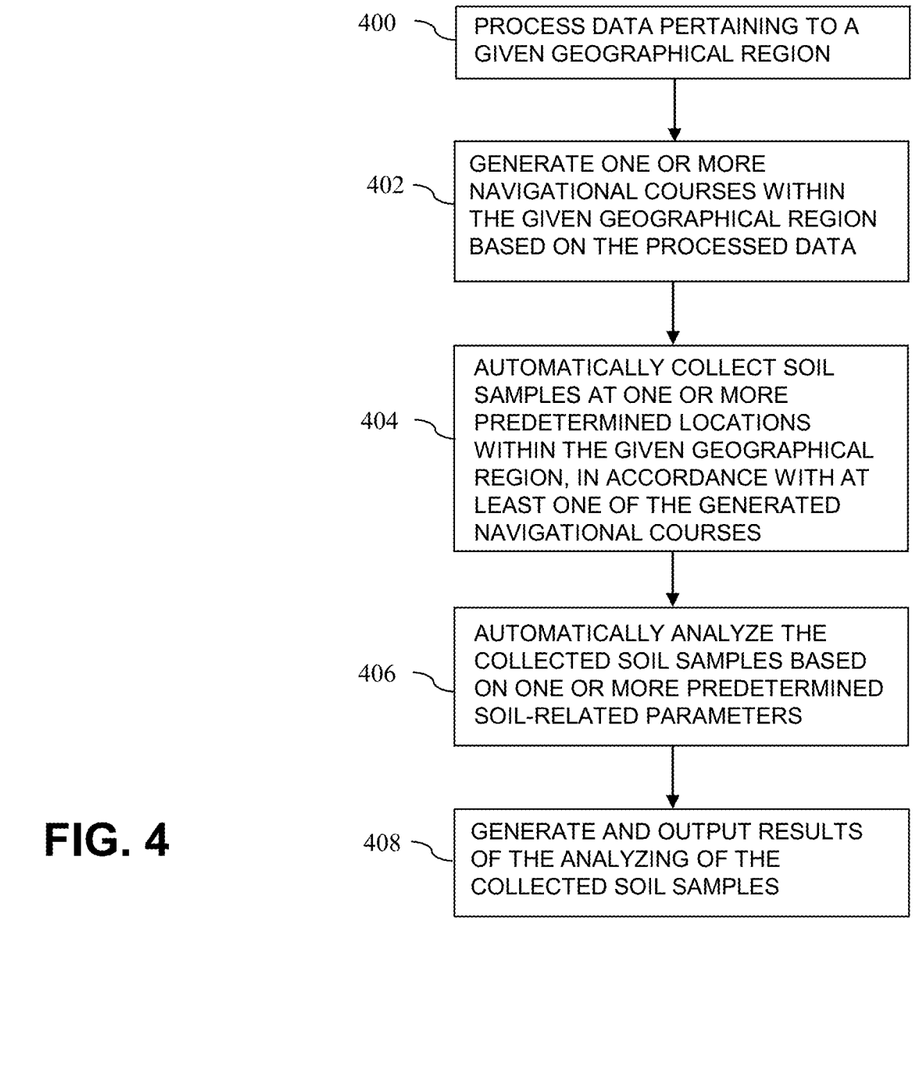
FIG. 4 is a flow diagram of a process for automated soil testing and analyses in an example embodiment.

FIG. 4 is a flow diagram of a process for automated soil testing and analyses in an example embodiment. In this embodiment, the process includes steps 400 through 408. These steps are assumed to be performed by the processor 120 utilizing its modules 130, 132 and 134.

Step 400 includes processing data pertaining to a given geographical region. The data pertaining to the given geographical region can include data detailing one or more sub-regions of the given geographical region, data detailing at least one of one or more hazards and one or more obstacles within the given geographical region, etc.

Step 402 includes generating one or more navigational courses within the given geographical region based at least in part on the processed data. The one or more navigation courses can include a grid and/or a path. Additionally, the one or more navigation courses can include an instruction to follow one or more pre-identified objects. Also, at least one embodiment includes automatically executing at least one of the generated navigational courses in accordance with at least one of a temporally-based schedule and one or more triggering events.

Step 404 includes automatically collecting one or more soil samples at one or more predetermined locations within the given geographical region, in accordance with at least one of the generated navigational courses. Automatically collecting the one or more soil samples includes implementing at least one of one or more probes and one or more sensors.

Step 406 includes automatically analyzing the one or more collected soil samples based on one or more predetermined soil-related parameters. The one or more predetermined soil-related parameters can include, for example, moisture, temperature, pH, phosphorus level, nitrogen level, potassium level, calcium level, etc.

Step 408 includes generating and outputting results of the analyzing of the one or more collected soil samples. At least one embodiment can include automatically generating one or more suggestions pertaining to modifying at least a portion of soil within the given geographical region based at least in part on (i) the analyzing of the one or more collected soil samples and (ii) one or more desired values of at least one of the one or more predetermined soil-related parameters. Additionally, one or more embodiments can include automatically initiating one or more resource-related systems within the given geographical region based at least in part on the analyzing of the one or more collected soil samples. The one or more resource-related systems can include one or more water-distribution systems (e.g., sprinklers), one or more fertilizer-distribution systems, and/or one or more fungicide-distribution systems.

Also, the techniques depicted in FIG. 4 can be initiated by at least one of a human user and a server. Further, at least one embodiment includes automatically operating (the robotic system) on a golf course during one or more daytime hours and one or more nighttime hours.

Additionally, in one or more embodiments, an exemplary robotic system includes one or more power components (e.g., one or more solar panels, one or more batteries, etc.), a drive train and steering system, one or more motors, at least one of one or more probes and one or more sensors, and a computing device comprises at least one processor operably coupled to a memory. Further one or more embodiments can also include one or more rotors. In the above-noted exemplary system, the computing device is configured for processing data pertaining to a given geographical region, generating one or more navigational courses within the given geographical region based at least in part on the processed data, and automatically collecting, via the at least one of the one or more probes and the one or more sensors, one or more soil samples at one or more predetermined locations within the given geographical region, in accordance with at least one of the generated navigational courses. Also, the computing device is further configured for automatically analyzing the one or more collected soil samples based on one or more predetermined soil-related parameters, and generating and outputting results of the analyzing of the one or more collected soil samples. In one or more embodiments, the computing device is further configured for automatically generating one or more suggestions pertaining to modifying at least a portion of soil within the given geographical region based at least in part on (i) the analyzing of the one or more collected soil samples and (ii) one or more desired values of at least one of the one or more predetermined soil-related parameters.

Such a robotic system can also include one or more rotors and/or one or more subsystems capable of enabling vertical flight of the robotic system, wherein the one or more rotors and/or the one or more subsystems modify the amount of mass and/or normal force that the robotic system applies to a ground surface, maintain, via control capabilities, one or more wheels of the robotic system in contact with the ground surface while in operation, and control a type of motion of the robotic system separate from one or more types of motion associated with the one or more wheels of the robotic system, wherein the type of motion controlled by the one or more rotors and/or the one or more subsystems comprises vertical flight.

Additionally, in one or more embodiments, the computing device of such a robotic system can be further configured for automatically operating on a golf course during one or more daytime hours and one or more nighttime hours, as well as automatically tracking proximity to (i) a ground surface and (ii) one or more obstacles and/or objects positioned on the ground surface via the one or more sensors.

Other techniques can be used in association with one or more embodiments. Accordingly, the particular processing operations and other network functionality described in conjunction with FIG. 4 are presented by way of illustrative example only, and should not be construed as limiting the scope of the invention in any way. For example, the ordering of the process steps may be varied in one or more other embodiments, or certain steps may be performed concurrently with one another rather than serially. Also, the process steps or subsets thereof may be repeated periodically in conjunction with respective distinct instances of robotic system soil testing operations with respect to different users.

The above-described example embodiments provide significant advantages relative to conventional approaches. For example, one or more embodiments can include temporally-efficient soil testing, wherein results can be generated and provided to a user significantly more quickly than conventional approaches, which often require weeks of time. Additionally, one or more embodiments can include increasing crop yield via the efficiency and accuracy of the robotic system, generating one or more suggestions pertaining to optimizing fertilization and/or watering practices, as well as highlighting one or more nutrients that may be lacking in particular portions of soil and generating suggestions for remedying such deficiencies. At least one embodiment also enables more efficient and/or effective usage of fungicide, in a manner that does not create over-usage or misuse.

It is to be appreciated that the foregoing advantages are illustrative of advantages provided in certain embodiments, and need not be present in other embodiments.

Additionally, the networks disclosed herein can be implemented, for example, using one or more processing platforms. Such a processing platform can include, by way of example, at least one processing device comprising a processor coupled to a memory. In one or more embodiments, portions of a network as disclosed herein can illustratively include cloud infrastructure. The cloud infrastructure, in at least one such embodiment, can include a plurality of containers implemented using container host devices, and/or can include container-based virtualization infrastructure configured to implement Docker containers or other types of Linux containers.

The cloud infrastructure can additionally or alternatively include other types of virtualization infrastructure such as virtual machines implemented using a hypervisor. Additionally, the underlying physical machines include one or more distributed processing platforms that include one or more storage systems.

Such cloud infrastructure as described above can, by way of example, represent at least a portion of one processing platform. Another example of such a processing platform can include, as similarly detailed above in connection with FIG. 1, a plurality of processing devices which communicate with one another over a network. As yet another processing platform example, portions of a given processing platform in one or more embodiments can include converged infrastructure.

The particular processing platforms described above are presented by way of example only, and a given network such as network 100 can include additional or alternative processing platforms, as well as numerous distinct processing platforms in any combination, with each such platform comprising one or more computers, servers, storage devices and/or other processing devices.

Further, in accordance with one or more embodiments, processing devices and other network components can communicate with one another using a variety of different communication protocols and associated communication media.

It should again be emphasized that the embodiments described herein are presented for purposes of illustration only. Many variations may be made in the particular arrangements shown. Moreover, the assumptions made herein in the context of describing one or more illustrative embodiments should not be construed as limitations or requirements of the invention, and need not apply in one or more other embodiments. Numerous other alternative embodiments within the scope of the appended claims will be readily apparent to those skilled in the art.

What is claimed is:

1. A computer-implemented method comprising:
processing data pertaining to a given geographical region, wherein processing data pertaining to the given geographical region comprises identifying and labeling multiple sub-regions of the given geographical region;
generating one or more navigational courses associated with one or more of the multiple sub-regions within the given geographical region based at least in part on the processed data;
automatically executing at least one of the one or more generated navigational courses in accordance with at least one temporally-based schedule associated with at least one of the one or more sub-regions of the given geographical regions;
automatically tracking, during execution of the at least one of the one or more generated navigational courses, proximity to (i) a ground surface and (ii) one or more obstacles positioned on the ground surface via one or more sensors;

automatically analyzing one or more soil samples, based at least in part on one or more predetermined soil-related parameters, at one or more predetermined locations within the at least one of the one or more sub-regions of the given geographical region, in accordance with the at least one of the one or more generated navigational courses, wherein automatically analyzing the one or more soil samples comprises analyzing, via at least one of the one or more sensors and one or more probes;

generating and outputting results of the analyzing of the one or more soil samples; and automatically generating one or more suggestions pertaining to modifying at least a portion of soil within the given geographical region based at least in part on (i) the analyzing of the one or more soil samples and (ii) one or more desired values of at least one of the one or more predetermined soil-related parameters, wherein automatically generating one or more suggestions comprises automatically generating one or more suggestions to run one or more sprinklers, for one or more suggested durations of time, in at least one of the multiple sub-regions, in accordance with one or more user-identified soil moisture levels;

wherein the method is carried out by at least one computing device.

2. The computer-implemented method of claim 1, wherein the data pertaining to the given geographical region comprise data detailing the one or more sub-regions of the given geographical region.

3. The computer-implemented method of claim 1, wherein the data pertaining to the given geographical region comprise data detailing at least one of one or more hazards and one or more obstacles within the given geographical region.

4. The computer-implemented method of claim 1, wherein the one or more navigational courses comprises an instruction to follow one or more pre-identified objects.

5. The computer-implemented method of claim 1, wherein the one or more navigational courses comprises at least one of a grid and a path.

6. The computer-implemented method of claim 1, wherein the one or more predetermined soil-related parameters comprise one or more of moisture, temperature, pH, phosphorus level, nitrogen level, potassium level, and calcium level.

7. The computer-implemented method of claim 1, comprising:

automatically initiating one or more resource-related systems within the given geographical region based at least in part on the analyzing of the one or more soil samples.

8. The computer-implemented method of claim 7, wherein the one or more resource-related systems comprise at least one of one or more water-distribution systems, one or more fertilizer-distribution systems, and one or more fungicide-distribution systems.

9. The computer-implemented method of claim 1, wherein the method is initiated by at least one of a human user and a server.

10. The computer-implemented method of claim 1, comprising:

automatically operating on a golf course during one or more daytime hours and one or more nighttime hours.

11. A computer program product comprising a computer readable storage medium having program instructions embodied therewith, the program instructions executable by a computing device to cause the computing device to:

process data pertaining to a given geographical region, wherein processing data pertaining to the given geographical region comprises identifying and labeling multiple sub-regions of the given geographical region;

generate one or more navigational courses associated with one or more of the multiple sub-regions within the given geographical region based at least in part on the processed data;

automatically execute at least one of the one or more generated navigational courses in accordance with at least one temporally-based schedule associated with at least one of the one or more sub-regions of the given geographical regions;

automatically track, during execution of the at least one of the one or more generated navigational courses, proximity to (i) a ground surface and (ii) one or more obstacles positioned on the ground surface via one or more sensors;

automatically analyze one or more soil samples, based at least in part on one or more predetermined soil-related parameters, at one or more predetermined locations within the at least one of the one or more sub-regions of the given geographical region, in accordance with the at least one of the one or more generated navigational courses, wherein automatically analyzing the one or more soil samples comprises analyzing, via at least one of the one or more sensors and one or more probes;

generate and output results of the analyzing of the one or more soil samples; and automatically generate one or more suggestions pertaining to modifying at least a portion of soil within the given geographical region based at least in part on (i) the analyzing of the one or more soil samples and (ii) one or more desired values of at least one of the one or more predetermined soil-related parameters, wherein automatically generating one or more suggestions comprises automatically generating one or more suggestions to run one or more sprinklers, for one or more suggested durations of time, in at least one of the multiple sub-regions, in accordance with one or more user-identified soil moisture levels.

12. The computer program product of claim 11, wherein the program instructions executable by the computing device further cause the computing device to:

automatically initiate one or more resource-related systems within the given geographical region based at least in part on the analyzing of the one or more soil samples.

13. A robotic system comprising:

power components comprising one or more solar panels and one or more batteries;

a drive train and steering system;

one or more motors;

one or more probes and one or more sensors;

one or more subsystems capable of:

controlling at least one type of vertical motion of the robotic system, wherein said controlling comprises modifying an amount of normal force that the robotic system applies to at least one ground surface, and wherein the at least one type of vertical motion controlled by the one or more subsystems comprises vertical flight of at least a portion of the robotic system;

a computing device comprises at least one processor operably coupled to a memory, wherein the computing device is configured for:
- processing data pertaining to a given geographical region, wherein processing data pertaining to the given geographical region comprises identifying and labeling multiple sub-regions of the given geographical region;
- generating one or more navigational courses associated with one or more of the multiple sub-regions within the given geographical region based at least in part on the processed data;
- automatically executing at least one of the one or more generated navigational courses in accordance with at least one temporally-based schedule associated with at least one of the one or more sub-regions of the given geographical regions;
- automatically tracking, during execution of the at least one of the one or more generated navigational courses, proximity to (i) a ground surface and (ii) one or more obstacles positioned on the ground surface via one or more sensors;
- automatically collecting, via at least one of the one or more probes and the one or more sensors, one or more soil samples at one or more predetermined locations within the at least one of the one or more sub-regions of the given geographical region, in accordance with the at least one of the generated navigational courses;
- automatically analyzing the one or more collected soil samples based on one or more predetermined soil-related parameters;
- generating and outputting results of the analyzing of the one or more collected soil samples; and
- automatically generating one or more suggestions pertaining to modifying at least a portion of soil within the given geographical region based at least in part on (i) the analyzing of the one or more collected soil samples and (ii) one or more desired values of at least one of the one or more predetermined soil-related parameters, wherein automatically generating one or more suggestions comprises automatically generating one or more suggestions to run one or more sprinklers, for one or more suggested durations of time, in at least one of the multiple sub-regions, in accordance with one or more user-identified soil moisture levels.

14. The robotic system of claim 13, wherein the computing device is further configured for:
- automatically operating on a golf course during one or more daytime hours and one or more nighttime hours.

15. The robotic system of claim 13, wherein the data pertaining to the given geographical region comprise data detailing at least one of one or more hazards and one or more obstacles within the given geographical region.

16. The robotic system of claim 13, wherein the one or more navigational courses comprises an instruction to follow one or more pre-identified objects.

17. The robotic system of claim 13, wherein the one or more navigational courses comprises at least one of a grid and a path.

18. The robotic system of claim 13, wherein the one or more predetermined soil-related parameters comprise one or more of moisture, temperature, pH, phosphorus level, nitrogen level, potassium level, and calcium level.

19. The robotic system of claim 13, wherein the computing device is further configured for:
- automatically initiating one or more resource-related systems within the given geographical region based at least in part on the analyzing of the one or more soil samples.

20. The robotic system of claim 19, wherein the one or more resource-related systems comprise at least one of one or more water-distribution systems, one or more fertilizer-distribution systems, and one or more fungicide-distribution systems.

\* \* \* \* \*